(12) United States Patent
Maruenda Paulino et al.

(10) Patent No.: US 9,259,245 B2
(45) Date of Patent: Feb. 16, 2016

(54) SURGICAL DEVICE FOR CORRECTING DEFORMATION OF THE SPINAL COLUMN

(75) Inventors: José Ignacio Maruenda Paulino, Valencia (ES); Philippe Laurito, Le Val (FR); Stéphane Le Roux, Lyons (FR)

(73) Assignee: SPINEWAY, Ecully (FR)

( * ) Notice: Subject to any disclaimer, the term of this patent is extended or adjusted under 35 U.S.C. 154(b) by 171 days.

(21) Appl. No.: 13/984,100

(22) PCT Filed: Feb. 13, 2012

(86) PCT No.: PCT/FR2012/050310
§ 371 (c)(1),
(2), (4) Date: Feb. 10, 2014

(87) PCT Pub. No.: WO2012/123655
PCT Pub. Date: Sep. 20, 2012

(65) Prior Publication Data
US 2015/0127053 A1 May 7, 2015

(30) Foreign Application Priority Data

Feb. 18, 2011 (FR) ...................................... 11 51331

(51) Int. Cl.
*A61B 17/70* (2006.01)
*A61B 19/00* (2006.01)

(52) U.S. Cl.
CPC ........... *A61B 17/7004* (2013.01); *A61B 17/708* (2013.01); *A61B 17/7085* (2013.01); *A61B 2019/307* (2013.01)

(58) Field of Classification Search
CPC ........... A61B 17/7074; A61B 17/7077; A61B 17/708; A61B 17/7079; A61B 17/7083; A61B 17/7085; A61B 17/7086; A61B 17/7088; A61B 17/7089
See application file for complete search history.

(56) References Cited

U.S. PATENT DOCUMENTS 7,749,232 B2 * 7/2010 Salerni .......................... 606/103
7,922,749 B2 * 4/2011 Dewey ............... A61B 17/7086
606/246

(Continued)

FOREIGN PATENT DOCUMENTS

| EP | 0699056 A1 | 3/1996 |
| FR | 2658416 A1 | 8/1991 |

(Continued)

OTHER PUBLICATIONS

International Search Report for PCT/FR2012/050310 dated Jun. 5, 2012.

*Primary Examiner* — Jerry Cumberledge
(74) *Attorney, Agent, or Firm* — Heslin Rothenberg Farley & Mesiti P.C.

(57) ABSTRACT

Surgical device for correcting deformation of the spinal column includes tubular elements for temporary attachment at pedicle screw heads connected by a curved implantable rod, and rods engaged through the elements to align them corresponding to the correction. Each tubular element has two independent portions coupled to outside of the heads; one end of each part having fittings coupling the portions together. The rods comprise an alignment rod and a handling rod, arranged in openings delimited by the portions to move parallel to an axis of the elements. The handling rod acting, as displaced, to simultaneously displace the curved rod, previously engaged into the openings, towards the heads. The handling rod being removed and then coupled to the outside of the elements arranged in alignment to remove the alignment rod and engage, inside each element, a member actuating a nut for fastening the curved rod in each head.

13 Claims, 11 Drawing Sheets

(56) References Cited

U.S. PATENT DOCUMENTS

| | | | |
|---|---|---|---|
| 8,500,741 B2 * | 8/2013 | Hansen | 606/86 A |
| 8,540,719 B2 * | 9/2013 | Peukert et al. | 606/86 A |
| 8,663,292 B2 * | 3/2014 | Dec | A61B 17/7091 606/279 |
| 8,992,536 B2 * | 3/2015 | Piza Vallespir et al. | 606/86 A |
| 9,011,449 B1 * | 4/2015 | Cochran | A61B 17/86 606/264 |
| 2005/0192579 A1 * | 9/2005 | Jackson | 606/72 |
| 2006/0264934 A1 * | 11/2006 | Fallin | 606/61 |
| 2006/0271050 A1 * | 11/2006 | Piza Vallespir | 606/61 |
| 2009/0005814 A1 | 1/2009 | Miller et al. | |
| 2009/0204159 A1 * | 8/2009 | Justis et al. | 606/323 |
| 2010/0049206 A1 * | 2/2010 | Biyani | 606/104 |
| 2012/0109208 A1 * | 5/2012 | Justis et al. | 606/264 |
| 2014/0052139 A1 * | 2/2014 | Manninen | 606/105 |
| 2014/0316475 A1 * | 10/2014 | Parikh | A61B 17/7083 606/86 A |
| 2015/0112392 A1 * | 4/2015 | Anand | A61B 17/7011 606/279 |
| 2015/0230836 A1 * | 8/2015 | Cochran | A61B 17/7086 606/86 A |

FOREIGN PATENT DOCUMENTS

| | | |
|---|---|---|
| WO | 2006104813 A2 | 10/2006 |
| WO | 2010047736 A1 | 4/2010 |

* cited by examiner

SURGICAL DEVICE FOR CORRECTING DEFORMATION OF THE SPINAL COLUMN

CROSS REFERENCE TO RELATED APPLICATIONS

This application is a national stage filing under section 371 of International Application No. PCT/FR2012/050310 filed on Feb. 13, 2012, and published in French on Sep. 20, 2012 as WO 2012/123655 A1 and claims priority of French application No. 1151331 filed on Feb. 18, 2011, the entire disclosure of these applications being hereby incorporated herein by reference.

BACKGROUND ART

The invention relates to the technical field of surgical instruments for correcting a deformation in the spinal column.

The invention has an especially advantageous application for scoliosis correction.

In the field of spinal osteosynthesis, it is perfectly well known to use pedicle screws having their heads, in the form of sockets, fitted for the assembly and the fastening of at least one connection rod for performing a distraction or a compression, and redefining the curvature.

Different technical solutions have been provided, as for example appears from the teachings of patents FR 2.658.413 and EP 0.699.056.

Whatever the technical solution selected to install the connection rods, it is necessary for the pedicle screw heads to be substantially aligned for the engagement of said rods into recesses in the screw heads.

Now in spine pathologies with a severe deformation type (such as scoliosis), the vertebrae are displaced in the three planes of space: rotation, translation, and tilting.

It thus appears to be necessary to be able to correct such a deformation of the spinal column with the objective of straightening up the vertebrae so that they can be aligned.

Here again, various technical solutions have been provided.

The basic concept of these different solutions is the use of tubes which are temporarily attached to the pedicle screw heads. The different tubes are thus attached perpendicularly to the column axis and are angularly shifted, given the column deformation. The tubes should thus be straightened up to be aligned in order to correct the rotation of the vertebrae, to correct the deformation of the spinal column.

The present invention more specifically relates to the basic correction principle defined, for example, in "SPINE" review, Volume 33, 2008 N° 14, pages 1588 to 1597, which principle has been protected by a patent, as appears from the teachings of document WO 2006/104813.

Mainly, rods are engaged through the different tubes by being progressively displaced from top to bottom to substantially align said tubes corresponding to the spinal column correction.

According to the state of the art, the tubes are fastened inside of the heads to enable the vertebrae to rotate, but do not enable to implant the final correction rod intended to connect, as indicated, the pedicle screw heads.

Indeed, according to the state of the art, after having lowered the rods introduced through several tubes, substantially perpendicularly to their generatrix, to achieve the alignment, the operator is forced to go to the other side of the spine, for example, on the concave side, if he has started the operation on the convex side. Once the implantable rod has been attached on the concave side, the operator has to disassemble the tubular elements to attach the implantable rod on the convex side.

It is thus necessary to operate in several steps, which has disadvantages. Indeed, the resulting loss of time, the need to assemble the implantable rod on the side opposite to that receiving the instruments for correcting the spine, causes a loss of correction.

The invention aims at overcoming these disadvantages in a simple, sure, efficient, and rational way.

The problem that the invention aims at solving is to be able, in one go, to intervene on one side of the column, for example, on the convex side, and then on the other side of the column, on the concave side, while carrying the double function of, on the one hand, straightening up the spinal bodies by means of tubular elements and, on the other hand, positioning the implantable rod and attaching it at the level of the pedicle screw heads, without having to disassemble said tubular elements, while aiming at determining the thoracic kyphosis-type curvature to be restored, in a sagittal plane.

BRIEF SUMMARY OF THE INVENTION

To solve such a problem, a surgical device for correcting a spinal column has been designed and developed, of the type comprising, in known fashion, tubular elements capable of being temporarily attached at the level of pedicle screw heads arranged to be connected by a curved implantable correction rod. Rods are engaged through the different tubular elements to be vertically displaced from top to bottom for the correction of said spine by translation, tilting and rotation of the vertebrae.

According to the invention, given the problem to solve, each tubular element is in two portions and is fitted to be coupled to the outside of the pedicle screw heads. The rods, one of which forms an alignment rod while the other forms a handling rod, are engaged into ports, with the ability to move perpendicularly to the axis of the semi-tubular elements. The handling rod is capable of acting, as it moves, on means for simultaneously displacing the curved rod, previously engaged into the ports under the alignment rod, towards the pedicle screw heads, said handling rod being intended to be removed and then coupled to the outside of the aligned semi-tubular elements, to enable the removal of the alignment rod and the engagement, into each tubular element, of a member for actuating a nut for fastening the curved rod in each of the pedicle screw heads.

These features thus enable, on the one hand, to correct the rotation of the vertebrae and to maintain the obtained correction and, on the other hand, to install the implantable rod, and then to lock said rod on the screws by fastening nuts introduced into the tubular correction elements without losing the relative position of said elements, and this, with no disassembly.

To solve the problem of coupling the tubular elements outside of the screw heads with the aim of totally freeing the inside of said heads, each tubular element is made of two independent portions, one of the ends of each portion having fittings for coupling said portions together and with respect to the corresponding pedicle screw head.

The coupling fittings are formed of two forks capable of being connected in jointed fashion, to enable to space apart the parts to position them with respect to the pedicle screw head, and then to push them back in order to clamp said head maintained between said portions by holding means.

To solve the problem of forming the tubular element as such, for the engagement of the different rods, the other end of each portion cooperates, after having been pushed back, with a hollow connection cap to form the tubular element as such, said portions delimiting the diametrically-opposite ports.

To solve the problem of installing the implantable curved rod by means of the handling rod engaged through several tubes with the ability of vertically moving from top to bottom, the means for displacing said implantable curved rod are a ring assembled with the ability to slide along the considered tubular element.

To solve the problem of angularly indexing the curved rod as it moves towards the pedicle screw heads, the ring has, at its base, diametrically-opposite recesses capable of being positioned opposite to the ports to cooperate with the section of the curved rod.

To solve the problem of positioning the alignment and handling rods, and their maintaining in waiting position, the recesses of the ring cooperate, before the displacement of said ring, with a locking stud, the alignment and handling rods being arranged above the ring, while the implantable curved rod is arranged under said ring.

To solve the problem of coupling, outside of the tubular elements, the handling rod, to clear the passage of the tightening nut, the end of each tubular element, opposite to its coupling with the pedicle screw head, receives an added mobile collar having a laterally-protruding portion for the engagement of the handling rod having been used to displace the ring and concomitantly, the implantable curved rod.

With the aim of determining the angular position of the vertebrae in a sagittal plane, especially to restore a physiological curvature, (thoracic kyphosis, lumbar lordosis) and to perfectly maintain in aligned position the different tubular elements, the latter are connected two by two at their free end, by spacing members.

To solve the problem of introducing a fastening nut into the pedicle screw head, for the fastening of the implantable curved rod, the pedicle screw head which has, in known fashion, a recess while forming a socket for the engagement of the curved rod, is continued, on either side of the recess, by breakable threaded tabs for the positioning of the nut in order to fasten the curved rod to the pedicle screw head.

According to another feature, the pedicle screw head is of one-piece or polyaxial type.

The invention also relates to the method for correcting a deformation of the spinal column, according to which:
- pedicle screws and tubular elements, formed in two portions to clamp the external surface of the screw heads, are first coupled;
- pedicle screws equipped with the tubular elements, which are used as a screwdriver capable of being disassembled and reused, are implanted;
- an alignment rod is transversely engaged through the different tubular elements easily aligned by hand to cause the alignment of said elements, corresponding to the spine correction after a rotation of the vertebrae;
- the different tubular elements are coupled by a spacer member;
- a handling rod capable of bearing against means assembled with the ability to move in guided fashion along the tubular element is transversely engaged under the alignment rod;
- an implantable curved rod intended to be fastened in the pedicle screw heads is transversely engaged under the element movable along the tube;
- a pressure is applied, in a motion directed from top to bottom on the handling rod, to cause the displacement of the means for enabling the simultaneous displacement of the curved rod and its positioning in the screw heads;
- the handling rod is removed and positioned in external fittings of each of the tubular elements;
- the alignment rod is removed;
- a nut and an actuating member are engaged inside of each tubular element to provide the fastening of the curved rod in each of the corresponding pedicle screw heads;
- the tubular elements are removed.

The spine being aligned by this implantation on one side (unilateral assembly), implants can be installed on the side of the spine left clear (bilateral assembly).

It may also be provided to install, either simultaneously, or one after the other, tube-screws on the other side of the vertebrae, whereby a bilateral symmetrical assembly will have been formed. Increasing the number of screws equipped with tubes for an identical number of vertebrae provides more control, less unit pressure on each screw/pedicle, given a distribution of forces between a larger number of tube-screws.

After having carried out the previously-described steps, and installed a curved rod in the pedicle screw heads maintained by non fully tightened tightening nuts (non blocked on said rod):
- The handling rod is removed (in the eyelets outside of the assembly).
- The alignment rod is removed.
- A new, shorter handling rod is inserted into the opening of the tubular elements.

The use of a shorter handling rod enables to attach a smaller number of tubular elements and of vertebrae, at the operator's choice during the operation. It is accordingly possible to handle certain vertebrae only, while maintaining others in fixed position.

For example, one or two tubular elements and vertebrae maintained fixed at each end of the assembly enable to form a fixed point with respect to which the operator can actuate the tubular elements of the center, attached together by a rod having a length exactly corresponding to the spacing of the tubular elements which are desired to be manipulated.

This corresponds to an aim of the surgical operation, which is to correct gibbosity, that is, a group of ribs, deformed more than the displacement of the vertebrae attached thereto would require, and which form a hump in the back.

It is thus possible to connect or to separate, as adapted to the gibbosity correction needs observed during the operation, groups of tube-screws-vertebrae, by varying the length of the handling rod.

BRIEF DESCRIPTION OF THE DRAWING FIGURES

The invention is discussed hereafter in further detail by means of the accompanying drawings, among which.

DETAILED DESCRIPTION

Figure 1:
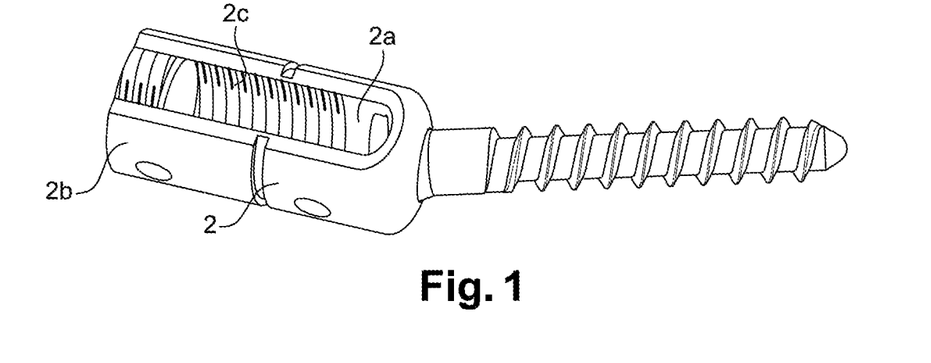
FIG. 1 is a perspective view of an example of pedicle screw head used with the surgical correction device according to the invention.
Figure 2:
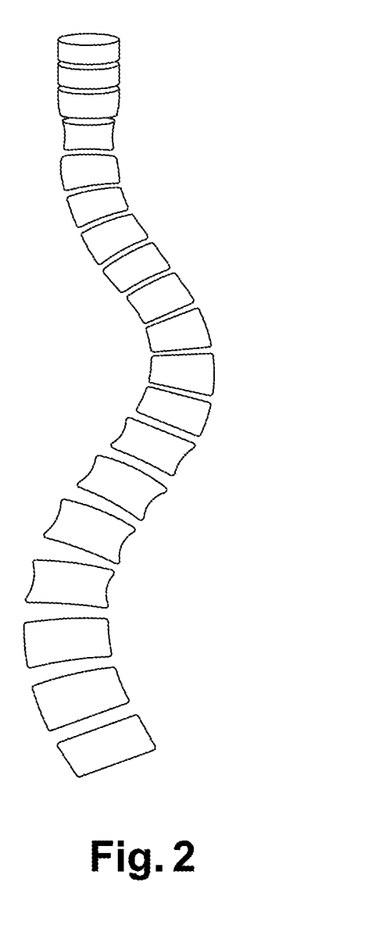
FIGS. 2 and 3 are purely schematic views showing a spine deformation in the form of a scoliosis before correction (FIG. 2) and after correction (FIG. 3)
Figure 3:
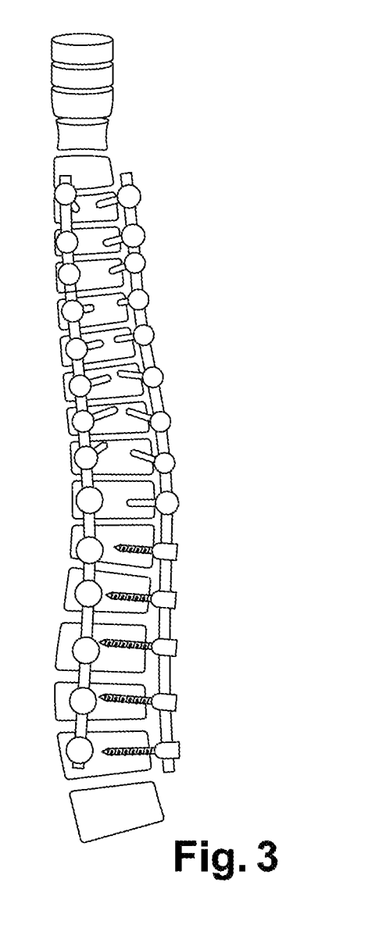

FIGS. 2 and 3 illustrate the spinal column correction principle. The shown deformation for example corresponds to a scoliosis. As indicated, the different vertebrae (V) are symbolized by cylinders.

It should be reminded, as known, that the surgical device for performing this correction comprises tubular elements (1) capable of being temporarily attached at the level of pedicle screw heads (2) arranged to be connected by a distraction or compression implantable curved rod (3). Rods (4) and (5) are intended to be engaged through the different tubular elements (1). Rod (4) thus forms an alignment rod for aligning the tubular elements (1), to provide the spinal column correction after a rotation, a translation, and a tilting, this in the three planes of space, of the vertebrae resulting from said alignment. Rod (5) forms a handling rod for the installation of implantable rod (3) in pedicle screw head (2).

It should be reminded that the aim of the invention is to be able to align the different tubular elements (1), resulting in the straightening up of the different vertebrae, and then, within the same operating time, with no disassembly, installing the implantable curved correction rod (3) in the different screw heads (2) and fastening said curved rod (3) in said screw heads (2). It should be noted that there is no loss of the obtained correction, the insertion of the curved rod occurs at the center of the tubular guiding elements.

According to a first feature, each tubular element (1) has fittings to be coupled to the outside of the pedicle screw heads (2).

It should be noted that the shape of the lower portion of each tubular element has a very large surface area of contact with the external surfaces of the screw head, which provides a significant interconnection and cohesion between the tubular elements and the screws, to displace, correct, and control the displacement of the position of the vertebrae to rectify their deformation.

Figure 22:
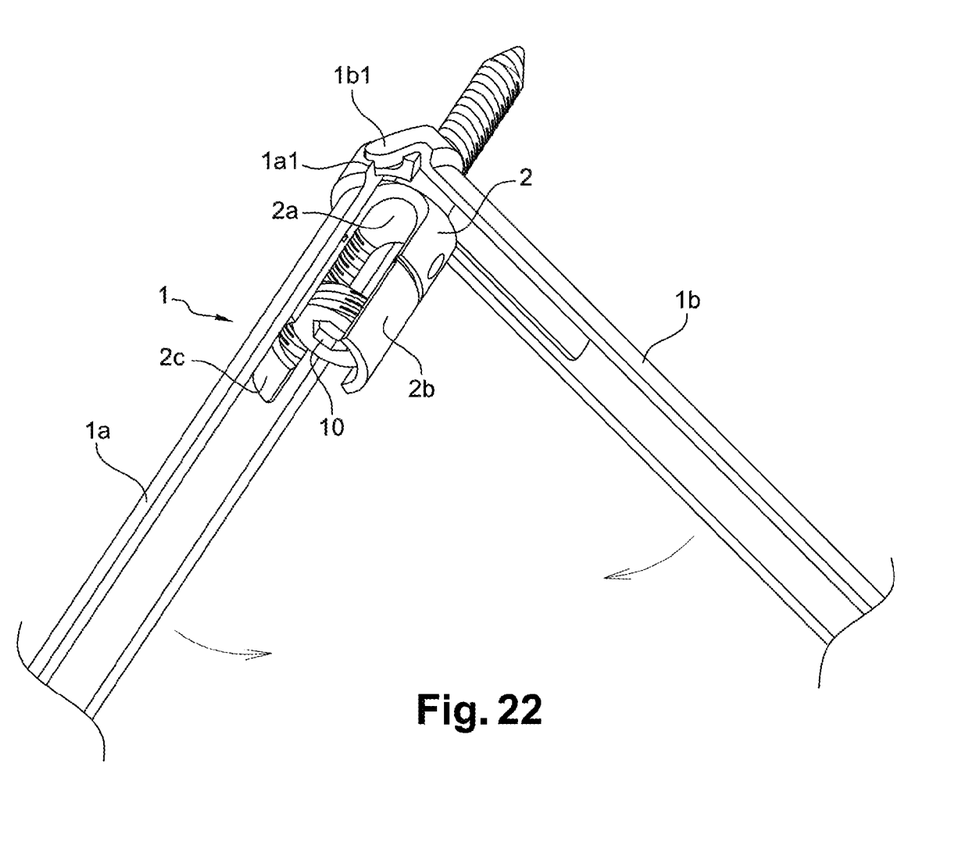
FIG. 22 is a perspective view showing the installation of the tubular element at the level of the pedicle screw head.

To achieve this, as shown in FIG. 22, each tubular element (1) is made of two independent portions (1a) and (1b). One of the ends of each portion (1a) and (1b) has fittings (1a1) and (1b1) provided to ensure the coupling, on the one hand, of the parts together and, on the other hand, with respect to the corresponding pedicle screw head (2). Such coupling fittings (1a1) and (1b1) are formed by two forks capable of being connected in jointed fashion. For example, the branches of one of the forks (1a1) have inner studs behaving as axes cooperating with recesses of the external surface of the branches of the other fork (1b1).

The coupling of the two portions (1a) and (1b), which thus are semi-tubular elements, is performed circularly at the contact with the external surface of the pedicle screw heads (2).

This enables to space apart portions (1a) and (1b) to position them with respect to pedicle screw head (2), and then to push them back to clamp said pedicle screw head. It should be noted that pedicle screw head (2) has holding fittings cooperating with complementary fittings of at least one of the other portions (1a) and (1b). For example, such fittings are formed by at least one lug or other indexing means of one of parts (1a) and (1b) close to fork (1a1) or (1b1) and capable of cooperating with a blind hole of a portion of the pedicle screw head (2).

The other end of each portion (1a) and (1b) cooperates, after having been pushed back, as indicated previously, with a hollow cap (6) capable of ensuring the connections to said portions to form the tubular element as such. After coupling of portions (1a) and (1b), as indicated, the latter delimit diametrically opposite openings (1c) and (1d).

Alignment and handling rods (4) and (5) are engaged into openings (1c) and (1d) with the ability to move perpendicularly to the axis of the tubular elements (1).

As will be indicated in the following description, the handling rod (5) is capable of acting, as it moves, on means (7) for simultaneously displacing the implantable curved rod (3) previously engaged into openings (1c) and (1d).

The means (7), for displacing said implantable curved rod (3) are a ring assembled with the ability to slide along the tubular element (1). This ring (7) ring has, at its base, diametrically opposite recesses (7a) capable of being positioned opposite to the openings (1c) and (1d) to cooperate with the section of the curved rod (3). This ensures the indexing of the curved rod (3), avoiding its rotating on itself as it moves.

It should also be noted that recesses (7a) of the ring (7) cooperate, after the displacement of said ring, with a stud possibly present on a portion of the tubular element (1) to lock said ring in position. Rods (4) and (5) are arranged above the rings (7) under the caps (6), while implantable curved rod (3) is arranged under said rings (7).

As a result, pressing on the rod (5) causes the displacement of the different rings (7) and accordingly of the implantable curved rod (3) through openings (1c) and (1d) of elements (1) until curved rod (3) is positioned in the corresponding pedicle screw heads (2). Such a positioning is possible given that the screw heads (2) are totally disengaged after the coupling and the alignment of the tubular elements (1), which are performed from the outside of said pedicle screw heads.

According to another important feature of the invention, the handling rod (5) is intended to be removed and coupled to the outside of the aligned tubular elements (1). For this purpose, the end of each tubular element (1), opposite to their coupling with pedicle screw heads (2), receives an added collar (8) having a laterally protruding portion (8a) for the engagement of the rod (5).

It should be noted that the different tubular elements (1) are connected two by two at their free end by a spacer member (9).

Spacer member (9) has a variable length, at the surgeon's choice; this length determines the distance between tubular elements, which results in displacing the vertebrae relative to one another; this enables the surgeon to control the curvature of the implanted spine section, and thereby to restore a physiological curvature (for example, thoracic kyphosis).

A range of different lengths is provided for the spacer members.

Each spacer member enables to attach together two contiguous tubular elements having a position forming an angle between them. Each spacer member is formed of a plate having two round holes, each provided with a ring forming a mobile pivoting joint inserted in the plate thickness. The holding occurs when the ring is slid along each tubular element.

As known, each pedicle screw head (2) is a bushing having a recess (2a) for the engagement of the implantable curved rod (3). According to the invention, the pedicle screw head (2) is continued on either side of recess (2a), by breakable tabs (2b) and (2c). In the same way as the bushing thread, tabs (2b) and (2c) are threaded for the installation of a nut (10) for the fastening of the rod (3) in the corresponding pedicle screw head.

Given the features forming the basis of the correction device according to the invention, the method is described hereafter in relation with FIGS. 4 to 20.

In each of the screw heads (2), tubular elements (1) are coupled in the previously-indicated conditions, that is, on the outside of the screw heads, to clear the inside of said screw heads.

The different pedicle screws with long winglets (2), equipped with the tubular elements (1), are fastened in the spinal bodies, for example, on the convex side. It should be noted that the pedicle screw heads may be one-piece or polyaxial, as perfectly well known by those skilled in the art.

Figure 4:
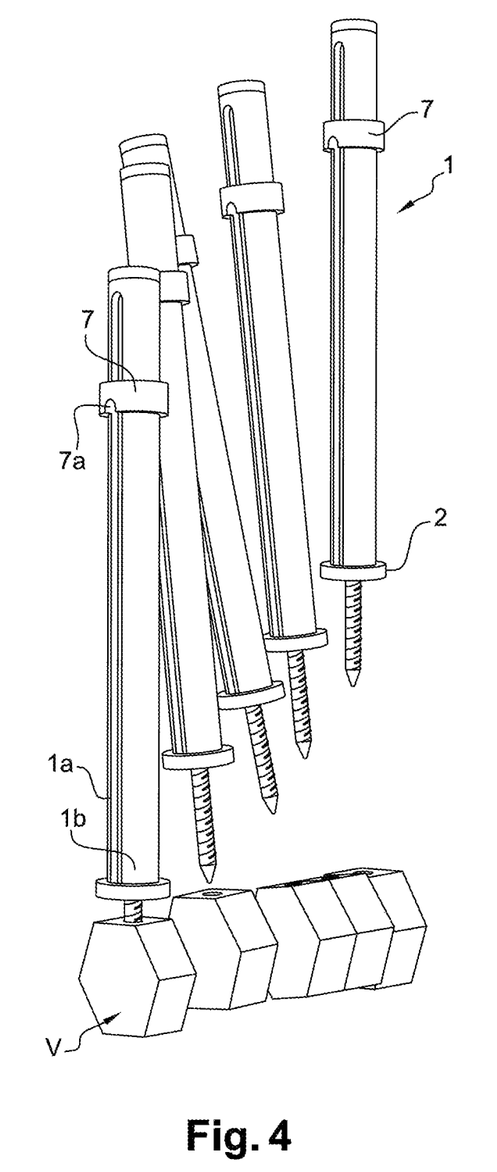
FIGS. 4 to 20 are perspective views showing the main steps of the correction of a spine by means of the surgical device according to the invention, the spine bodies of said spine being symbolized by cylinders.
Figure 5:
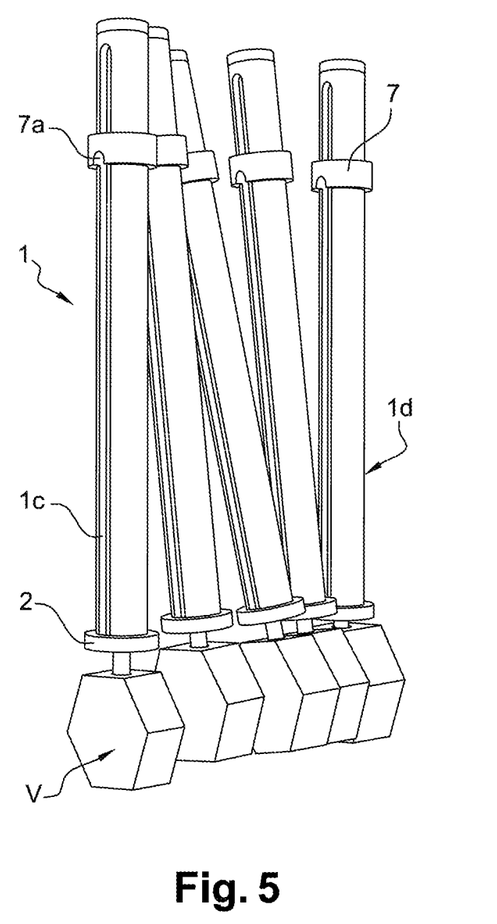

Each tubular element (1) is then equipped with its cap (fastening nut) (6). The ring (7) is positioned in the upper portion of the considered tubular element. At this stage, the tubular elements (1) are angularly shifted in correspondence with the spine deformation (FIGS. 4 and 5). The collars (8) are also arranged in the upper portion of the tubular elements (FIG. 6).

Figures 6, 7:
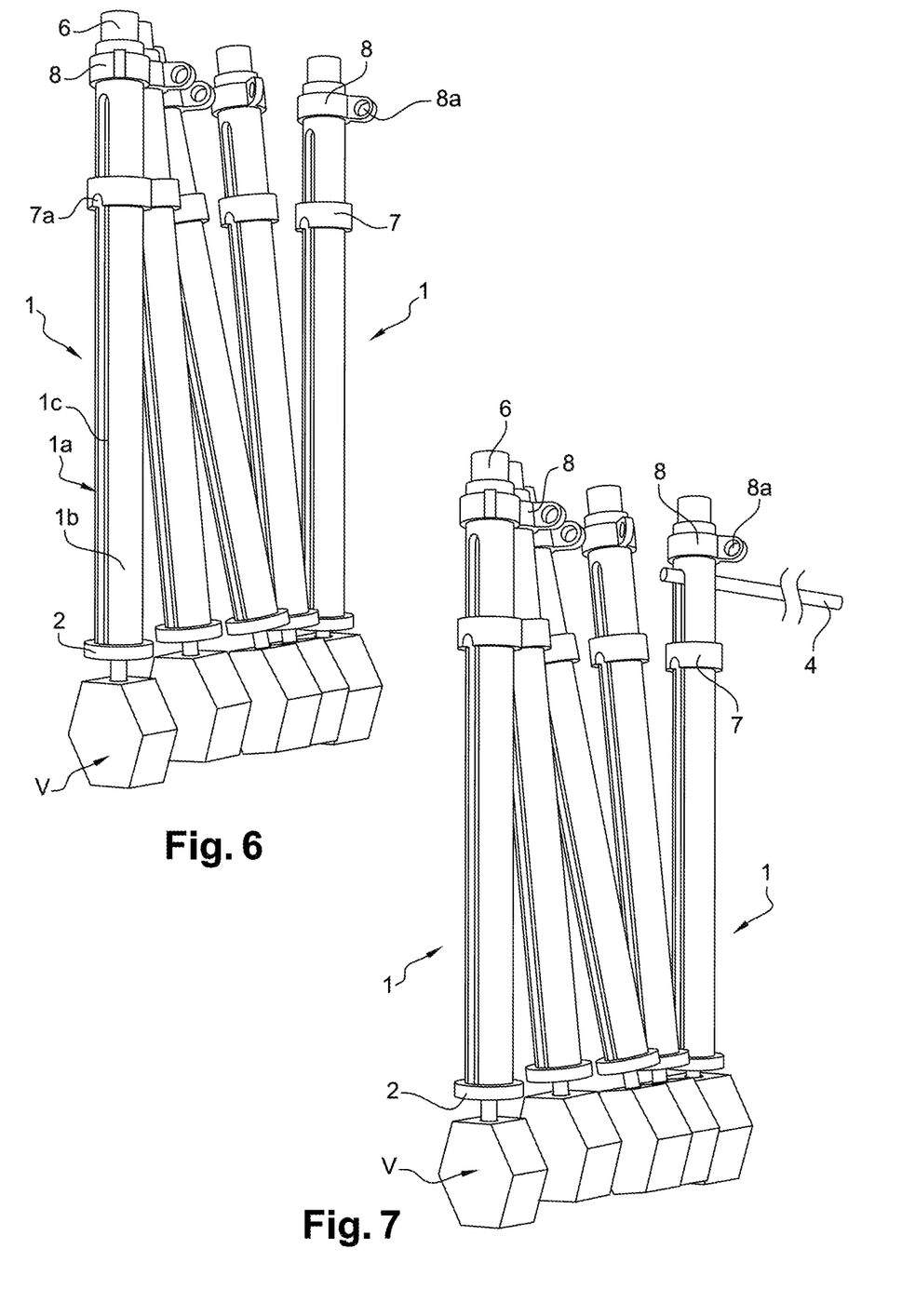
Figures 8, 9:
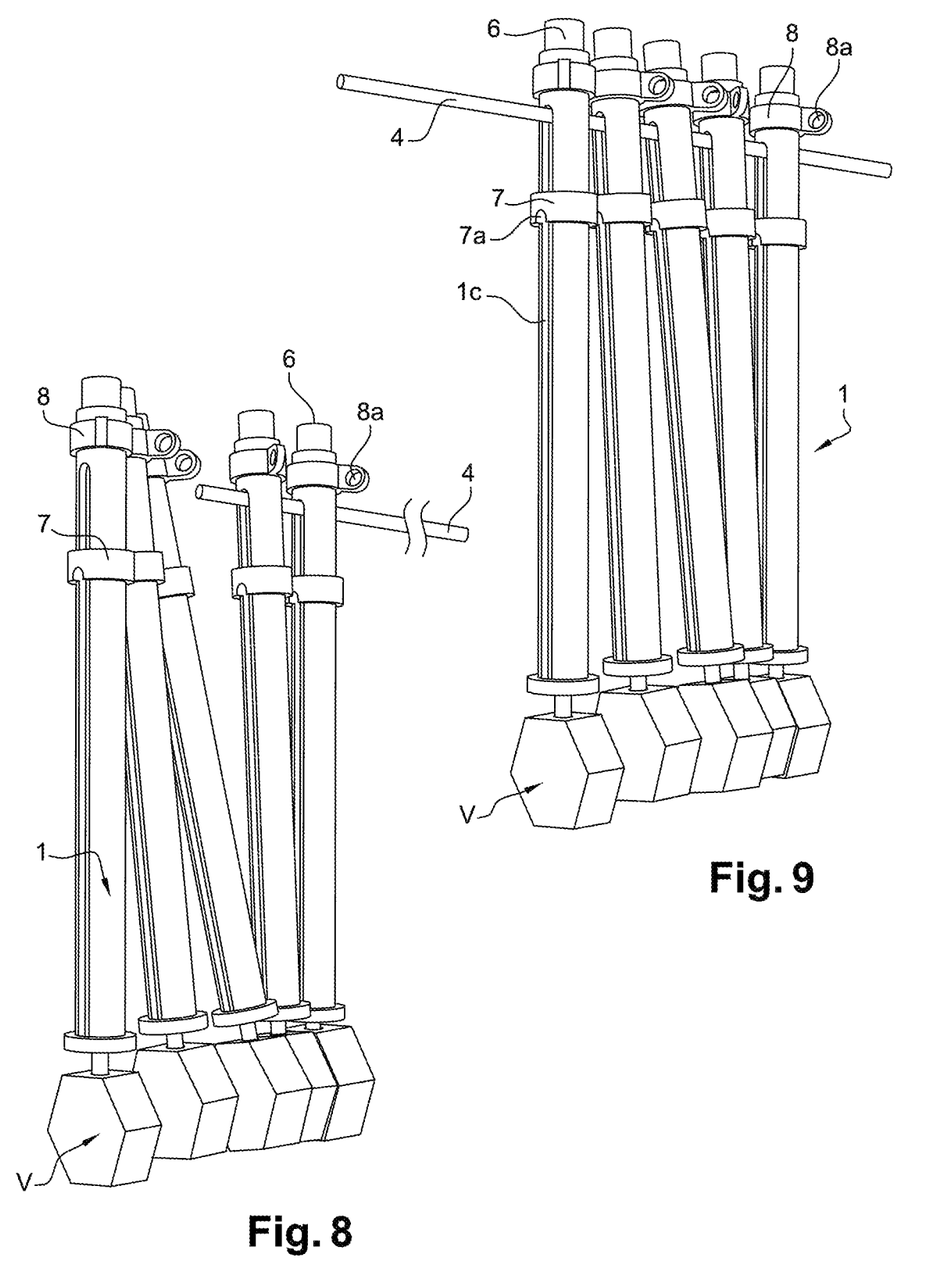
Figure 10:
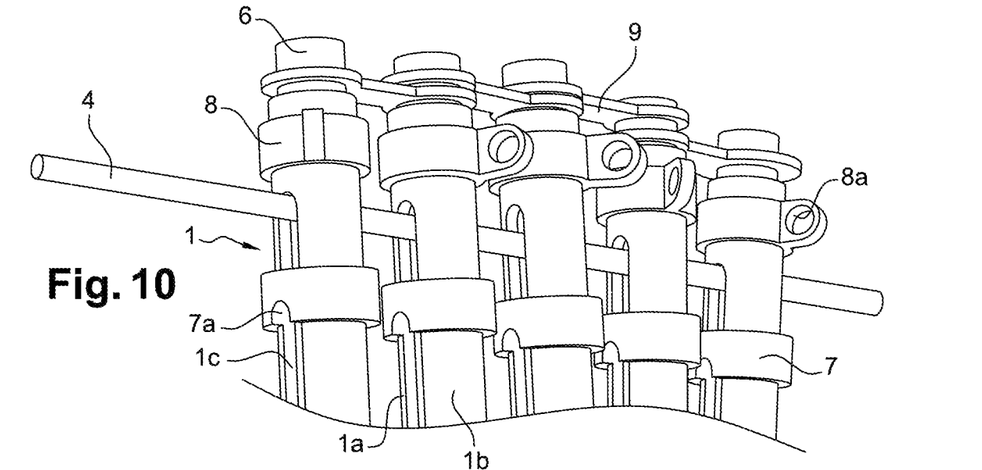

The rod (4) is then engaged through openings (1c) and (1d) of the different tubular elements (1) to cause their progressive straightening up in order to align them by generating a translation, a tilting, and a rotation of the vertebrae for the spine correction (FIGS. 7, 8, and 9).

The different tubular elements (1) are then coupled two by two by the spacer members (9) (FIG. 10) to predetermine the expected curvature correction, such as a thoracic kyphosis, for example.

Figure 11:
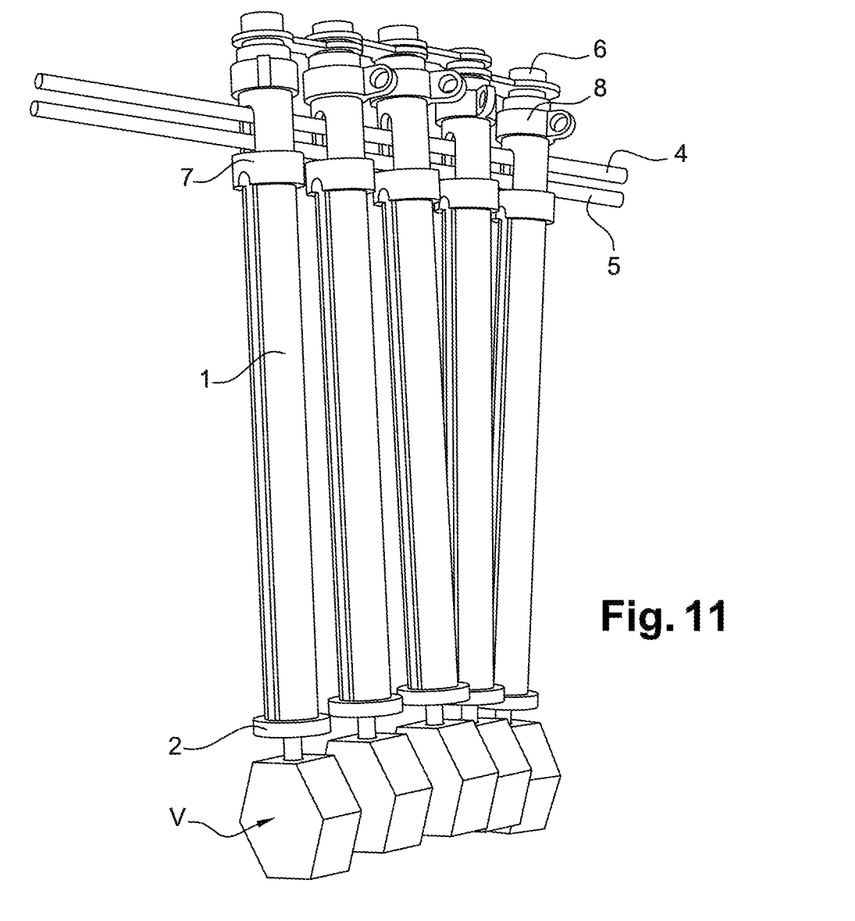
Figure 12:
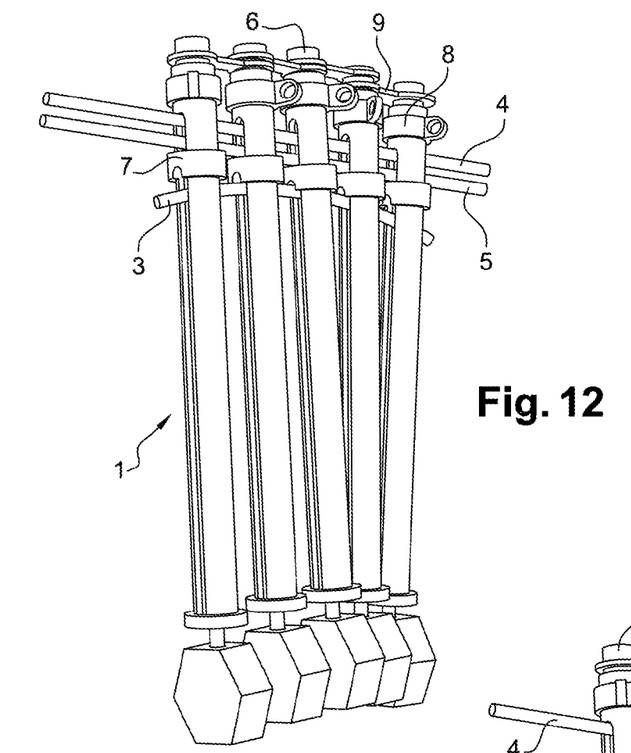

Under alignment rod (4) is transversely engaged the handling rod (5) capable of bearing against the rings (7) (FIG. 11).

Figure 13:
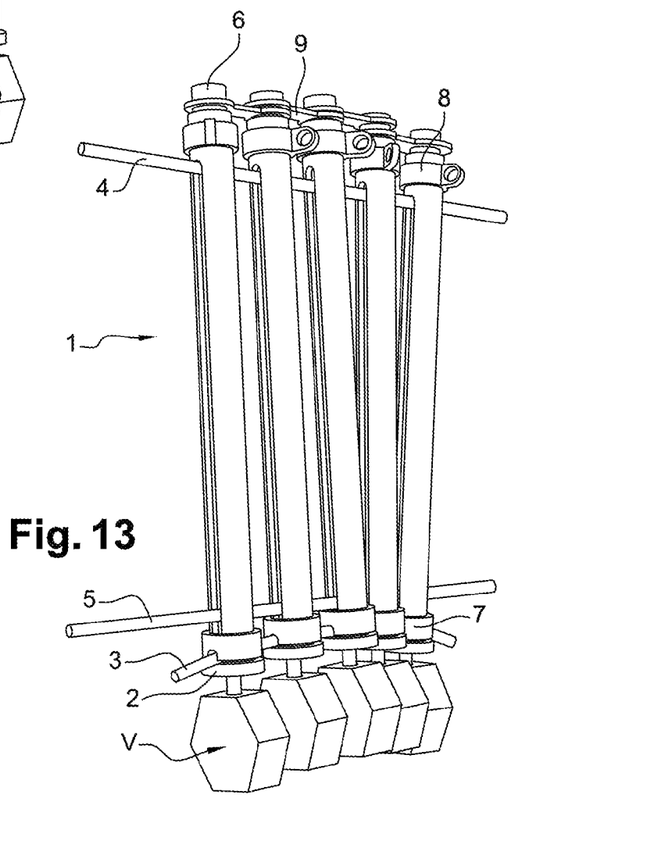

Under rings (5) (FIG. 12), is transversely engaged implantable curved rod (3) to be positioned and fastened in pedicle screw heads (2a). For this purpose, a pressure is applied, according to a motion from top to bottom, to handling rod (5) to cause the displacement of the different rings (7) and the simultaneous displacement of the curved rod (3) until it positions in the recesses of the sockets of the pedicle screw heads (FIG. 13).

Figures 14, 15:
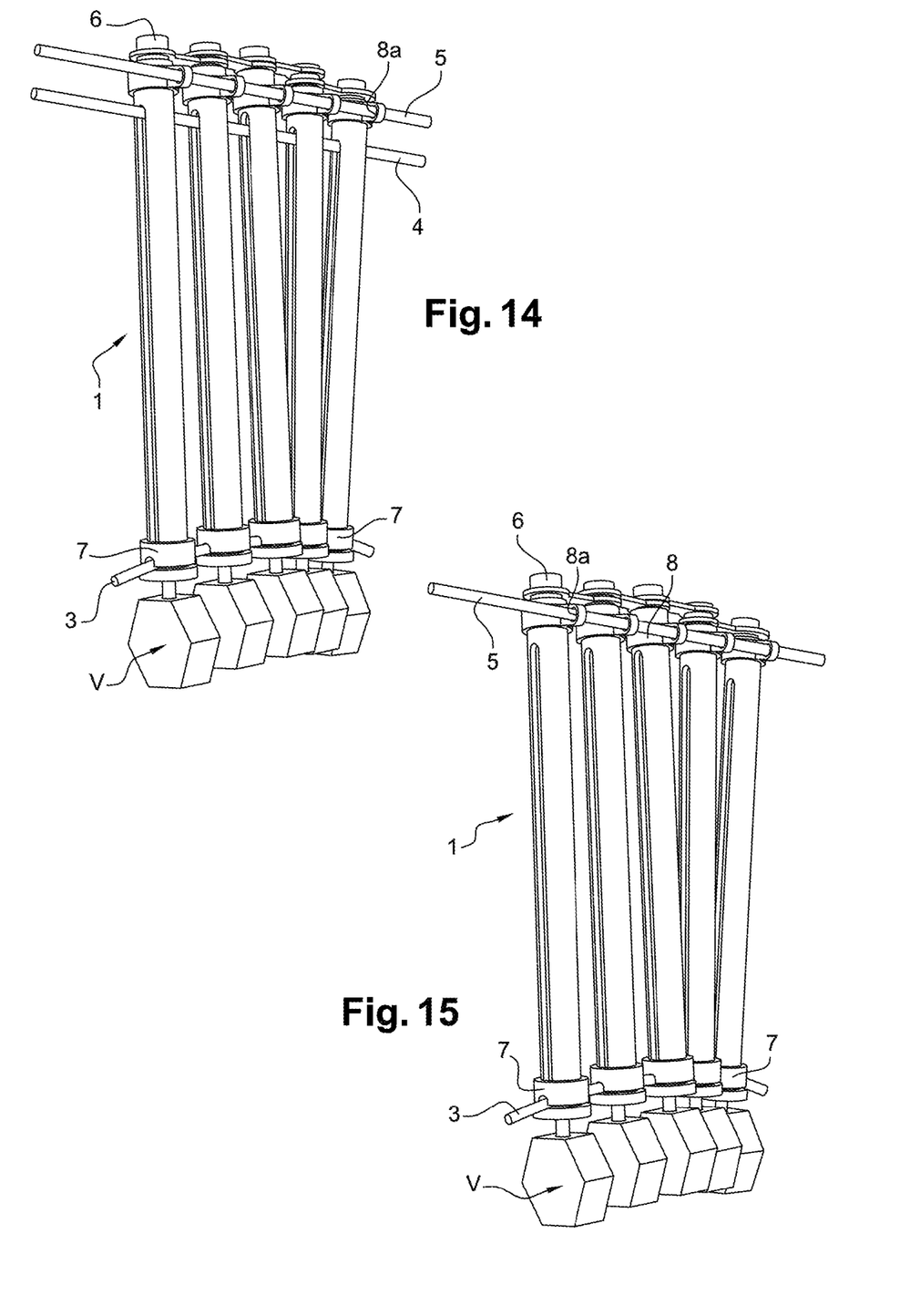

Handling rod (5) is then removed to be positioned in the different collars (8), that is, outside of tubular elements (1) (FIG. 14). It is then possible to remove alignment rod (4) given that the present spine curvature correction is maintained by handling rod (5) arranged outside of the tubular elements, as indicated (FIG. 15).

Figures 16, 17:
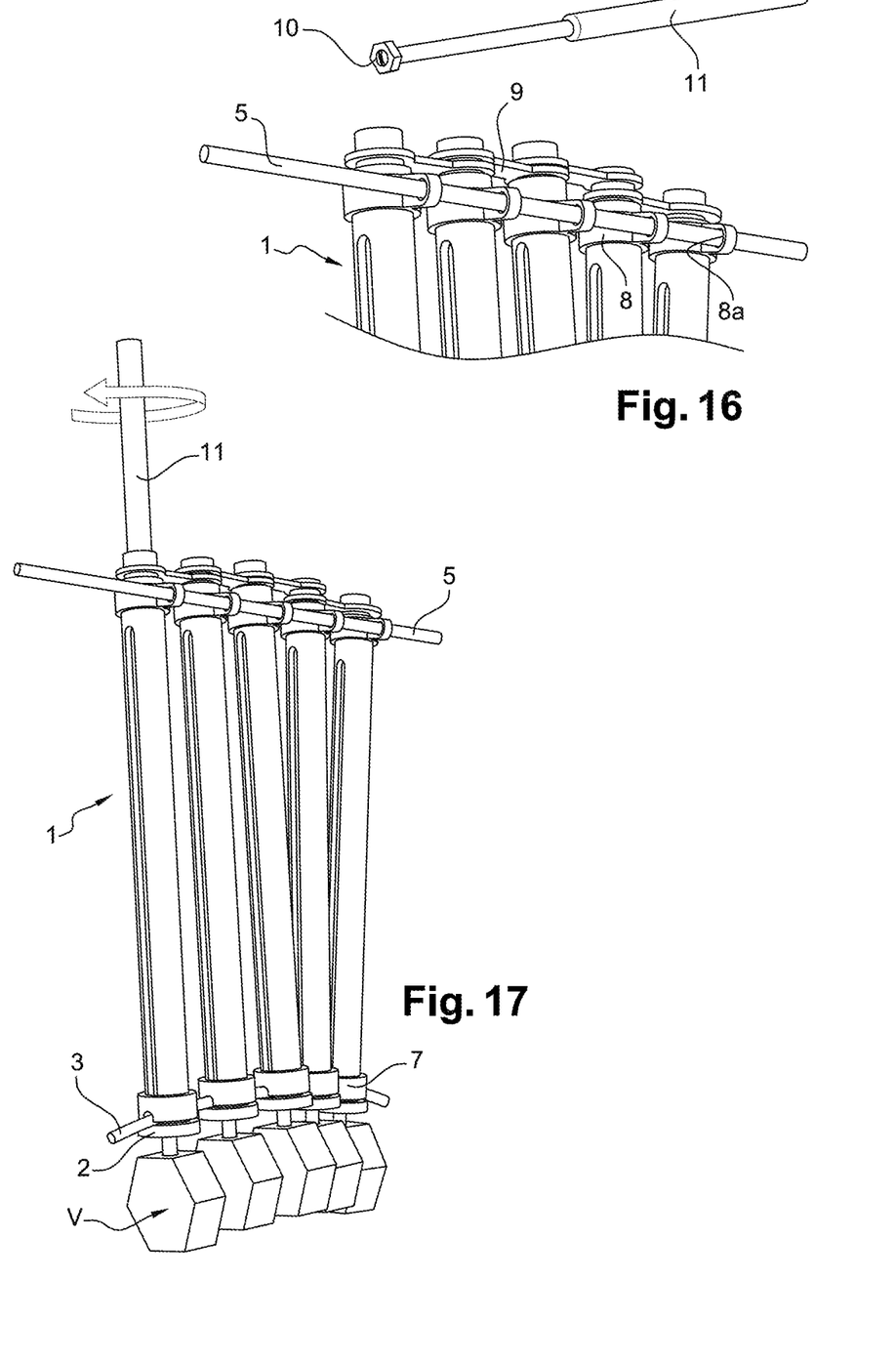

As a result, the inside of the different tubular elements (1) and of the pedicle screw heads (2), is totally free, accordingly enabling to introduce nuts (10) through the different tubular elements (1) by an appropriate actuation member (11) (FIG. 16) and to screw the nuts (10) in the pedicle screw heads to provide the fastening of implantable rod (3) (FIG. 17).

Figures 18, 19:
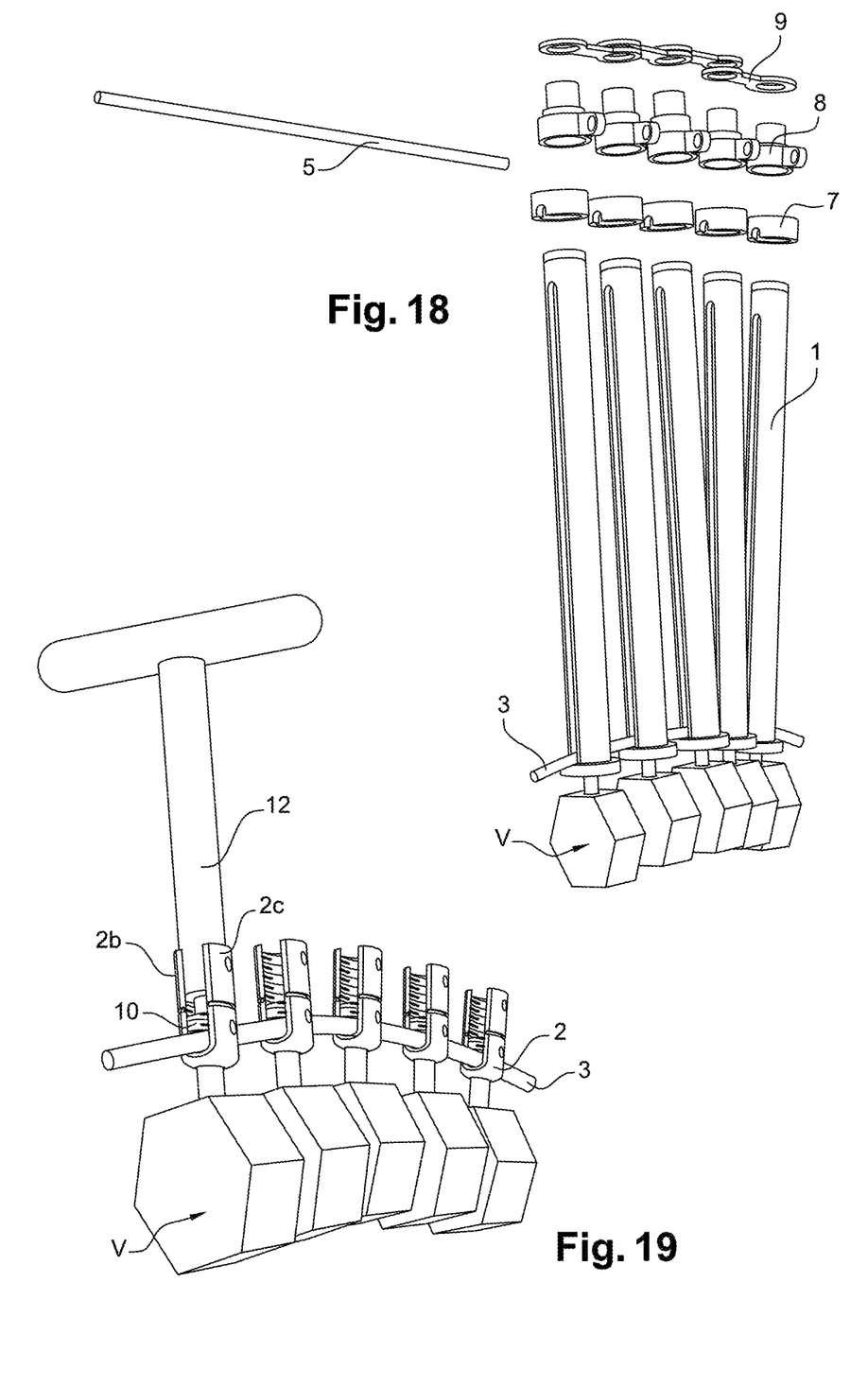

At this stage of the operating mode, it is then possible to disassemble the device and, accordingly, to remove the tubular elements (FIG. 18).

Figure 20:
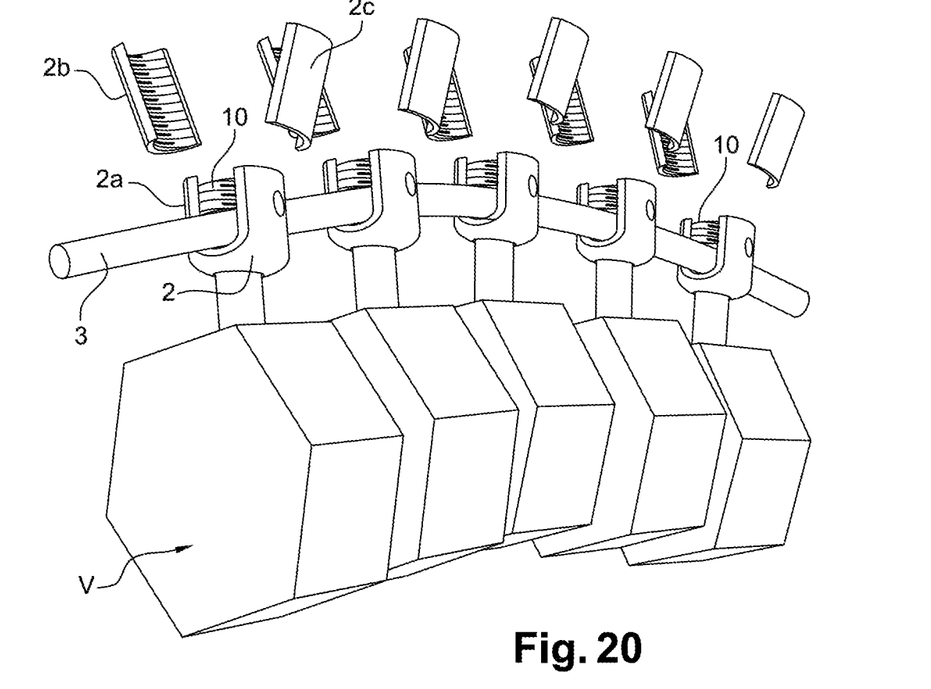

It is then sufficient to fully screw the nuts (10) by means of a member (12) for connecting and definitively fastening the curved rod (3) in pedicle screw heads (2) (FIG. 19), to break breakable portions (2b) and (2c) of the pedicle screws (2) (FIG. 20).

Figure 21:
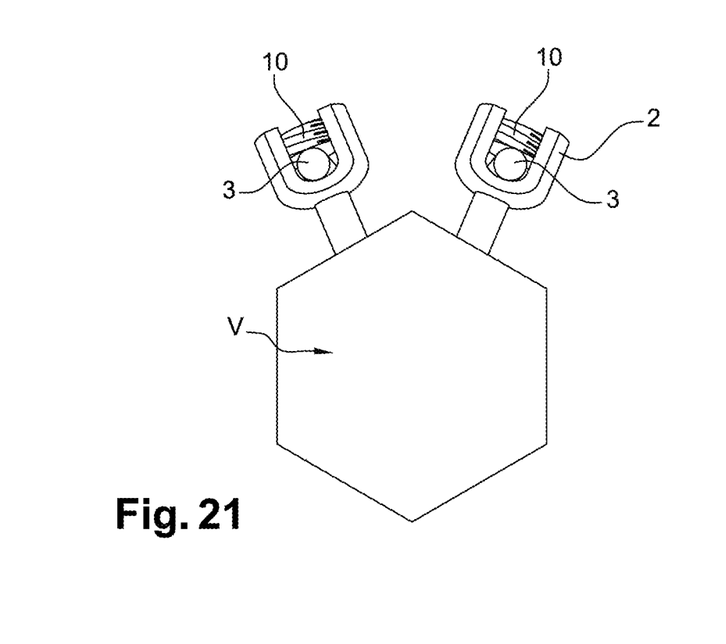
FIG. 21 is a simplified view showing the installation of the device on both sides of the spine.

It is then possible to follow the same line of operation from the convex side (FIG. 21).

The advantages well appear from the description, in particular, it should be underlined and it is reminded that each side of the spine is corrected in a single go, by straightening up the vertebrae, and then by installing the implantable curved rod and fastening it, without having to disassemble the correction device thus enabling, not only to gain time, but also to avoid losing the correction.

It should also be noted that the spacer members, between the different tubes, are very important, especially to restore a kyphosis, enabling the surgeon to adjust the tube spacing and, accordingly, to act on said kyphosis.

While remaining within the spirit and scope of the invention, a symmetrical use may be provided, that is, two instrumented sides for a better efficiency of the correction force. Means for connecting the sides by horizontally connecting the tubular elements or rods on each side may also be devised.

Similarly, a use with a mini-invasive percutaneous approach path may be devised: the incisions made on the skin are limited to the diameter of each tubular element, the handling rod being introduced from top to bottom all the way to the contact with the skin the position of the vertebrae is corrected "under the skin".

A distant incision may be made, upwards or downwards of the line formed by the assembly of tubular elements, and the curved implant rod is slid under the skin until it reaches the inside of said elements and of the screw heads (final position of the implant rod).

The invention claimed is:

1. A surgical device for correcting a deformation of the spinal column, the surgical device comprising: an implantable curved rod, pedicle screw heads arranged to be connected by the curved rod, tubular elements adapted for being temporarily attached at a level of the pedicle screw heads, an alignment rod and a handling rod engaged through the tubular elements to align the tubular elements corresponding to correction of a spine, by translation, tilting, and rotation of vertebrae, wherein each tubular element is formed of two independent semi-tubular portions adapted to be coupled to an outside of the pedicle screw heads and delimit diametrically opposite openings in the tubular elements, wherein a remote first end of each of the independent semi-tubular portions has fittings for coupling said independent semi-tubular portions to each other in jointed fashion beneath a corresponding one of the pedicle screw heads, wherein the implantable curved rod, the alignment rod and the handling rod are arranged in the diametrically opposite openings with the ability to move parallel to an axis of the tubular elements, spacer means being slideable along at least one of the tubular elements and mounted between the handling rod and the implantable curved rod, wherein when the handling rod is displaced downwardly and pushes on said spacer means, the implantable curved rod is simultaneously displaced towards the pedicle screw heads, and a plurality of nuts for fastening the curved rod in the pedicle screw heads, wherein the tubular elements are adapted for receiving, each in turn, an actuating member engaged therein, following removal of the alignment rod and the handling rod from the diametrically opposite openings in the tubular elements, for screwing a nut of said plurality in each of the pedicle screw heads, each nut in turn, thus fastening the curved rod in each of the pedicle screw heads.

2. The surgical device of claim 1, wherein the coupling fittings at the remote first end comprise two forks connected in jointed fashion, to enable to space apart the independent semi-tubular portions to position each of the independent semi-tubular portions with respect to the corresponding one of the pedicle screw heads, and then to push the independent semi-tubular portions back together in order to clamp said corresponding one of the pedicle screw heads maintained between said independent semi-tubular portions by holding means.

3. The surgical device of claim 2, further comprising a hollow connection nut for each tubular element, wherein after the independent semi-tubular portions have been pushed back together, a second end of each of the independent semi-tubular portions opposite to the remote first end cooperates with the hollow connection nut to form the tubular elements.

4. The surgical device of claim 1, wherein the spacer means comprises at least one ring slideable along at least one of the tubular elements.

5. The surgical device of claim 4, wherein a base of the at least one ring has diametrically opposite recesses positioned opposite to the diametrically opposite openings to cooperate with the curved rod.

6. The surgical device of claim 5, further comprising a position locking stud, wherein before displacement of the at least one ring along the tubular element, the diametrically opposite recesses of the at least one ring cooperate with the position locking stud, and the alignment rod and the handling rod are arranged above the at least one ring, while the implantable curved rod is arranged below the at least one ring.

7. The surgical device of claim 4, wherein a second end of each of the independent semi-tubular portions opposite to the remote first end receives an added collar having a laterally protruding portion for engagement of the handling rod after the removal of the handling rod from the diametrically opposite openings in the tubular elements.

8. The surgical device of claim 1, wherein each pedicle screw head has a recess forming a socket for engagement of the implantable curved rod, said pedicle screw head being continued, on either side of the recess, by breakable tapered tabs for the positioning of the nut to fasten the curved rod in the corresponding pedicle screw head.

9. The surgical device of claim 8, wherein the pedicle screw head is of one-piece or polyaxial type.

10. The surgical device of claim 1, wherein the tubular elements are connected two by two at their free end by spacer members.

11. The surgical device of claim 10, wherein each spacer member comprises a plate having two round holes.

12. The surgical device of claim 1, in combination with said actuating member.

13. A method for correcting a deformation of the spinal column employing pedicle screws and the surgical device of claim 1, comprising:
    coupling the pedicle screws and the tubular elements to clamp the external surface of the pedicle screw heads;
    implanting the pedicle screws equipped with the tubular elements in vertebrae of a spine;
    transversely engaging the alignment rod through the diametrically opposite openings in the tubular elements to cause alignment of the tubular elements corresponding to a desired spine correction after rotation of the vertebrae;
    transversely engaging the handling rod through the diametrically opposite openings in the tubular elements above the spacer means;
    transversely engaging the implantable curved rod through the diametrically opposite openings in the tubular elements below the spacer means;
    applying downward motion to the handling rod to cause displacement of the spacer means and simultaneous displacement of the implantable curved rod into the pedicle screw heads;
    removal of the handling rod from the diametrically opposite openings in the tubular elements, and positioning of the handling rod in external fittings of each of the tubular elements;
    removal of the alignment rod from the diametrically opposite openings in the tubular elements;
    engaging a nut and an actuating member inside of each of the tubular elements to fasten the implantable curved rod in the pedicle screw heads; and
    removal of the tubular elements.

* * * * *